(12) United States Patent
Drott et al.

(10) Patent No.: US 12,059,502 B2
(45) Date of Patent: Aug. 13, 2024

(54) COMPOSITION AND METHOD FOR PRETREATING CANCER

(71) Applicant: Valcuria AB, Lund (SE)

(72) Inventors: Johan Drott, Bjärred (SE); Kristina Drott, Lund (SE); Stefan Ulvenlund, Lund (SE); Catharina Salomonsson, Lund (SE)

(73) Assignee: VALCURIA AB, Lund (SE)

( * ) Notice: Subject to any disclaimer, the term of this patent is extended or adjusted under 35 U.S.C. 154(b) by 191 days.

(21) Appl. No.: 16/087,034

(22) PCT Filed: Apr. 21, 2017

(86) PCT No.: PCT/EP2017/059480
§ 371 (c)(1),
(2) Date: Sep. 20, 2018

(87) PCT Pub. No.: WO2017/182611
PCT Pub. Date: Oct. 26, 2017

(65) Prior Publication Data
US 2019/0099380 A1 Apr. 4, 2019

(30) Foreign Application Priority Data
Apr. 21, 2016 (EP) .................................... 16166455

(51) Int. Cl.
| | |
|---|---|
| *A61K 9/50* | (2006.01) |
| *A61K 31/19* | (2006.01) |
| *A61K 31/20* | (2006.01) |
| *A61K 31/573* | (2006.01) |
| *A61K 45/06* | (2006.01) |
| *A61K 47/38* | (2006.01) |
| *A61P 35/00* | (2006.01) |

(52) U.S. Cl.
CPC .......... *A61K 9/5084* (2013.01); *A61K 9/5026* (2013.01); *A61K 9/5047* (2013.01); *A61K 31/19* (2013.01); *A61K 31/20* (2013.01); *A61K 31/573* (2013.01); *A61K 45/06* (2013.01); *A61K 47/38* (2013.01); *A61P 35/00* (2018.01)

(58) Field of Classification Search
CPC .... A61K 31/573; A61K 47/38; A61K 9/5026; A61K 9/5047; A61K 9/5084; A61K 31/20; A61K 31/19; A61K 45/06; A61K 2300/00; A61P 35/00
See application file for complete search history.

(56) References Cited

U.S. PATENT DOCUMENTS

| | | | | |
|---|---|---|---|---|
| 2007/0232528 | A1* | 10/2007 | Franke .................. | A61K 9/5084 514/254.09 |
| 2008/0234265 | A1 | 9/2008 | Witta et al. | |
| 2011/0008426 | A1* | 1/2011 | Jain ........................ | A61K 9/209 424/457 |
| 2011/0177165 | A1 | 7/2011 | Gerber et al. | |
| 2013/0022677 | A1* | 1/2013 | Mullen ................ | A61K 9/2013 424/465 |
| 2014/0093565 | A1* | 4/2014 | Drott ...................... | A61K 38/07 424/474 |
| 2014/0127291 | A1* | 5/2014 | Morella ............... | A61K 9/0095 424/458 |

FOREIGN PATENT DOCUMENTS

| | | |
|---|---|---|
| EP | 1591109 | 11/2005 |
| JP | 2007535518 A | 12/2007 |
| WO | WO 2005/105055 A1 | 11/2005 |
| WO | WO 2012/128709 | 9/2012 |
| WO | WO 2013/039488 | 3/2013 |
| WO | WO 2014/079922 | 5/2014 |

OTHER PUBLICATIONS

Batvoska et al. Biosci. Biotechnolog. Biochem., 2008, 72(10): 2623-2631 (Year: 2008).*

(Continued)

*Primary Examiner* — Doan T Phan
(74) *Attorney, Agent, or Firm* — James S. Keddie; Bozicevic, Field & Francis LLP (57) ABSTRACT

The present invention relates to a pharmaceutical composition comprising an HDAC inhibitor, a pharmaceutically acceptable acid or salt thereof or a mixture of the acid and salt, provided both in a immediate release form and in an extended release form wherein 70-90 weight % of the HDAC inhibitor is provided in the immediate release form and the remainder of the HDAC inhibitor is provided in the extended release form. In further aspects the present invention relates to a kit comprising a number of doses of an HDAC inhibitor, a pharmaceutically acceptable acid or salt thereof or a mixture of the acid and salt thereof provided both in an immediate release form and in an extended release form. In still further aspects the present invention relates to an HDAC inhibitor, a pharmaceutically acceptable acid or salt thereof or a mixture of the acid and salt, provided in both an immediate release form and an extended release form, for use in a method of pretreating cancer, and a method of pretreating cancer using said HDAC inhibitor provided both in said immediate release form and said extended release form. Further aspects relate to combination treatment of cancer and to a dispenser for a blister pack.

20 Claims, 6 Drawing Sheets

(56) References Cited

OTHER PUBLICATIONS

Anonymous (edited by Aulton et al.), "Aulton's Pharmaceutics: The Design and Manufacture of Medicines", Elsevier, 2013, XP002770565, pp. 578-580.
Dokmanovic et al., "Histone Deacetylase Inhibitors: Overview and Perspectives", Molecular Cancer Research, American Association for Cancer Research, 2007, 5(10): 981-989.
Morrison, "Evolution of R-CHOP therapy for older patients with diffuse large B-cell lymphoma", Expert Rev. Anticancer Ther., 2008, 8(10): 1651-1658.
Ji et al., "Regulation of the Interaction of Inosine Monophosphate Dehydrogenase with Mycophenolic Acid by GTP", The Journal of Biological Chemistry, 2006, 281(1): 206-212.
Pubchem description for Mycophenolate mofetil (ID#5281078), downloaded from the internet on Nov. 3, 2021.
Pubchem description for Mycophenolic acid (ID#446541), downloaded from the internet on Nov. 3, 2021.
Pubchem description for Valproic acid (ID#3121), downloaded from the internet on Nov. 3, 2021.
Atmaca et al., "Valproic acid (VPA) in patients with refractory advanced cancer: a dose escalating phase I clinical trial", British Journal of Cancer, 2007, 97: 177-182.

\* cited by examiner

COMPOSITION AND METHOD FOR PRETREATING CANCER

CROSS-REFERENCE TO RELATED APPLICATIONS

This application is a § 371 national phase of International Application No. PCT/EP2017/059480, filed on Apr. 21, 2017, which claims the benefit of European Patent Application No. 16166455.2, filed on Apr. 21, 2016, which applications are incorporated by reference herein.

FIELD OF INVENTION

The invention relates to the field of compositions and methods of pretreating cancer, i.e. where one or more compositions is administered to an individual in need of cancer treatment as a pretreatment prior to other treatments to enhance the effect, or mitigate the side-effects, of the treatments.

BACKGROUND OF INVENTION

Cancer can be defined as an abnormal growth of cells which exhibit signs of uncontrolled proliferation and disturbed programmed cell death. From a classical view, sequential genetic events lead to malignant transformation, resulting in a cell clone that does not respect the integrity of other cells and tissues, and may eventually metastasize. Cancer can involve any tissue of the body and have many different forms in each body area.

Malignant lymphoma can be defined as a malignant transformation of the lymphatic cells of the hematopoietic system. Lymphomas can be divided into aggressive lymphomas and indolent lymphomas. Aggressive lymphomas are characterized by a rapid growth pattern, and can have dramatic clinical features. However, aggressive lymphomas can reach a complete cure by treatment with chemotherapy, radiotherapy and monoclonal antibodies. In contrast, indolent lymphomas (e.g., follicular lymphomas) have a slow growth pattern, and usually a more modest clinical presentation. However, although indolent lymphomas cannot reach a complete cure by standard lymphoma treatment, they can sometimes be cured by allogeneic stem cell transplantation. The median survival time for follicular lymphomas is 8-10 years. Diffuse Large B Cell Lymphoma and Hodgkin lymphoma belong to the group of aggressive lymphomas, while follicular lymphoma and chronic lymphocytic leukaemia are indolent lymphomas. Myelomas consist of malignantly transformed plasmacells. They are related to indolent lymphomas, but are usually considered an entity of their own. The prognosis is pessimistic, with a median survival time of 5-7 years.

One of the most frequent subtypes of malignant lymphoma is Diffuse Large B-cell Lymphoma (DLBCL) with an incidence of about 500 cases/year in Sweden. DLBCLs constitute 60-70% of the group of aggressive lymphomas. The median age at diagnosis is 70 years, and DLBCL is slightly more common in males than in females.

Standard first line treatment of DLBCL is chemotherapy consisting of a combination of cyclophosphamide, doxorubicin, vincristine and prednisone (CHOP). During recent years addition of the CD20 antibody rituximab has become international clinical standard (R-CHOP), leading to improved progression-free, event-free, disease-free and overall survival (Morrison, *Expert Rev Anticancer Ther,* 2008; 8(10): pp. 1651-1658). Still, since as many as 45% of patients die from their disease, there is a pronounced clinical need to increase progression-free survival in DLBCL patients.

One important field in the study of cancer diseases is the regulation of DNA transcription. This is a complex process and the mechanisms involved are only partially known. Histone Deacetylases (HDACs) can regulate expression of tumour suppressor genes and activities of transcription factors involved in both cancer initiation and progression. HDACs act through alteration of either DNA or the structural components of chromatin by histone deacetylation, thus affecting the three dimensional conformation of DNA without changing or interrupting its sequence (epigenetic modifications). It has also been suggested that they may alter the sensitivity to DNA damaging chemotherapy through modulation of chromatin structure. Along these lines, several in vitro studies have suggested that inhibition of HDACs can synergize with chemotherapy.

Therefore numerous HDAC inhibitors have been developed during the recent years. They can be divided into four classes; hydroxamic acids/carbamic acids, cyclic peptides, aliphatic acids and benzamides. Examples of HDAC inhibitors which have been approved for treatment of cancer include vorinostat and romidepsin which are approved for the treatment of cutaneous T-cell lymphoma lymphoma by the FDA (Food and drug administration), and which are currently evaluated in the treatment of other malignancies.

The clinically most well-known HDAC inhibitor is the anticonvulsant valproic acid, which has been utilized in the treatment of epilepsy since the 1970s. Valproic acid belongs to the aliphatic acid class of inhibitors.

The present inventors have previously, see WO2012/128709, shown that HDAC inhibitors in combination with steroids are useful when being administered to a human in need of cancer treatment as a pretreatment prior to other treatments, the result being that the effect of the treatment is enhanced.

Despite the promise of more effective treatment of cancer made by the advent of pretreatment using a HDAC inhibitor as taught by WO2012/128709, there are still difficulties to overcome to more fully realize the potential of cancer pretreatment using an HDAC inhibitor.

One difficulty that arises is that of how to most effectively administer the HDAC inhibitor to meet the requirements of a pretreatment use of the HDAC inhibitor. While some HDAC inhibitors, in particular Valproic acid, has been seen clinical use since the 1970, this clinical use has been related to a different medical field, i.e. that of treating of epilepsy, than the new field of pretreatment for cancer. Consequently earlier obtained knowledge of how to administer a HDAC inhibitor need not be the most effective when a HDAC inhibitor is administered as a pretreatment for cancer.

SUMMARY OF THE INVENTION

The invention relates to the finding that a plasma concentration of a HDAC inhibitor suitable for pretreatment of cancer can be obtained by a pharmaceutical composition comprising the HDAC inhibitor both in an immediate release form and in an extended release form. 70-90 weight % of the HDAC inhibitor is provided in the immediate release form and the remainder of the HDAC inhibitor is provided in the extended release form. The release of the HDAC inhibitor from the two release forms in the composition yields a plasma concentration profile which quickly reaches the desired concentration and maintains a plasma concentration at or above the desired concentration for at least 48 hours. Twice or thrice a day administration of the composition allows this desired concentration to be maintained and reaching the desired concentration quickly allows for performing the pretreatment in close connection, such as a few days before, the treatment to limit the exposure of the human to the composition to minimize side effects. This differs significantly from the earlier reported clinical use of HDAC inhibitors where a long period of up to 14 days or more has been needed or accepted in order to reach a desired concentration of the HDAC inhibitor. Such a long period would however be inefficient when the HDAC inhibitor is used for pretreating cancer and the prior art teachings in this field has therefore hitherto prevented or hindered realizing the potential of cancer pretreatment using an HDAC inhibitor.

Thus in a first aspect the present invention relates to a pharmaceutical composition comprising an HDAC inhibitor, a pharmaceutically acceptable acid or salt thereof or a mixture of the acid and salt, provided both in a immediate release form and in an extended release form wherein 70-90 weight % of the HDAC inhibitor is provided in the immediate release form and the remainder of the HDAC inhibitor is provided in the extended release form.

In a second aspect the invention relates to a device comprising the composition according to the first aspect of the present invention.

In a third aspect the invention relates to a kit comprising a number of doses of an HDAC inhibitor, a pharmaceutically acceptable acid or salt thereof or a mixture of the acid and salt thereof provided both in an immediate release form and in an extended release form. The kit is useful for providing and maintaining an effective concentration of the HDAC inhibitor during one session of pretreating cancer.

In a fourth aspect the invention relates to an HDAC inhibitor, a pharmaceutically acceptable acid or salt thereof or a mixture of the acid and salt, provided both in an immediate release form and in an extended release form, for use in a method of pretreating of cancer In a fifth aspect the invention relates to a method of pretreating cancer comprising administering an HDAC inhibitor, a pharmaceutically acceptable acid or salt thereof or a mixture of the acid and salt, provided both in an immediate release form and in an extended release form to a human suffering from cancer.

In a sixth aspect the invention relates to an HDAC inhibitor, a pharmaceutically acceptable acid or salt thereof or a mixture of the acid and salt, provided both in a immediate release form and in an extended release form, in combination with one or more chemotherapeutic or immunotherapeutic compositions, for use in a method of combination treatment of cancer In a seventh aspect the invention relates to a method of combination treatment of cancer comprising performing the method of pretreating cancer according to the fifth aspect of the present invention before performing one or more treatments of cancer.

In order for the pretreatment to be effective it is important that the human suffering from cancer is compliant in taking the pharmaceutical composition according to the first aspect of the present invention as intended or prescribed in order to obtain a suitable dose of the HDAC inhibitor.

Such compliance is ensured, or at least simplified, by the eight aspect of the present invention which relates to a dispenser for dispensing pharmaceuticals from a blister pack comprising a plurality of collapsible blisters sealed by a frangible sealing sheet, the dispenser comprising:

a lower housing portion comprising a plurality of apertures, and an upper housing portion joined to the lower housing part, the upper housing part comprising an elongated aperture defining a serpentine track sequentially running past each aperture of said plurality of apertures, whereby the lower housing portion and the upper housing portion define, between them, a cavity configured for receiving a blister pack such that the sealing sheet is oriented towards the lower housing portion and such that the blisters are oriented towards the upper housing portion and aligned with the plurality of apertures, the dispenser further comprising:

a press part extending from within the cavity to outside the cavity through the elongated aperture in the upper housing part, the press part being configured for being moveable along the serpentine track for sequentially physically striking and collapsing said plurality of blisters of said blister pack when said blister pack is received in said cavity.

DETAILED DESCRIPTION OF THE INVENTION

A first aspect of the present invention relates to a pharmaceutical composition comprising an HDAC inhibitor, a pharmaceutically acceptable acid or a salt thereof or a mixture of the acid and the salt, provided in both an immediate release form and in an extended release form wherein 70-90 weight % of the HDAC inhibitor is provided in the immediate release form and the remainder of the HDAC inhibitor is provided in the extended release form.

By providing the HDAC inhibitor, the pharmaceutically acceptable acid or salt thereof or the mixture of the acid and salt thereof in both the immediate release form and the extended release form, the combined release of the HDAC inhibitor quickly provide at least a desired concentration in the plasma of a human patient to which the pharmaceutical composition according to the first aspect of the present invention is administered to, this desired concentration then being maintained for a period of time.

In the context of the present invention pharmaceutically acceptable means that the entity referred to should be non-toxic.

In the context of the present invention any reference to the HDAC inhibitor is to be understood as covering also the pharmaceutically acceptable acid or salt of the HDAC inhibitor or the mixture of the acid and salt of the HDAC inhibitor.

In the context of the present invention the term immediate release form encompasses the term immediate release phase.

In the context of the present invention the term extended release form encompasses the terms sustained release form, extended release phase, and sustained release phase.

It is to be understood that the HDAC inhibitor may be the same in both the immediate release form and the extended release form, or that alternatively the HDAC inhibitor may be different in the immediate release form and the extended release form.

The immediate release form may for example release at least 50%, such as at least 75%, such as at least 90, 95 or 99%, of the HDAC inhibitor provided in the immediate release form within 30 minutes of the composition being administered to, or taken by, a human suffering from cancer.

The immediate release form may for example release 50% of the HDAC inhibitor provided in the immediate release form within 4-12 minutes, such as within 7 minutes when placed in PBS at 37° C. and pH 6.8 using a USP 711 device.

The extended release form may for example release less than 40%, such as less than 33%, such as less than 25%, such as less than 20%, such as 15, 12.5, 10, 8.125, 5% or 4% of the HDAC inhibitor in the extended release form within 30 minutes of the composition being administered to, or taken by, a human suffering from cancer.

The extended release form may for example release at the most 50%, such as 50% of the HDAC inhibitor provided in the extended release form within 120-220 minutes, such as within 170 minutes when placed in PBS at 37° C. and pH 6.8 using a USP 711 device.

Typically the time at which the extended release form has released 50% of the HDAC inhibitor is 10-20 times longer than the time at which the immediate release form has released 50% of the HDAC inhibitor. The amount of the immediate and extended release forms need not be equal, rather the immediate release form may have a larger volume and/or weight than the extended release form or vice versa.

In one embodiment of the pharmaceutical composition according to the first aspect of the present invention 1-99 weight % of the HDAC inhibitor is provided in the immediate release form and the remainder of the HDAC inhibitor is provided in the extended release form.

In other embodiments of the pharmaceutical composition according to the first aspect of the present invention 10 to 90 weight %, such as 20 to 80 weight %, such as 25 to 75 weight %, such as 30 to 70 weight %, such as 40 to 60 weight %, such as 45 to 55 weight %, such as 50% weight % of the HDAC inhibitor is provided in the immediate release form and the remainder of the HDAC inhibitor is provided in the extended release form.

Preferably 50 to 90 weight %, such as 75 weight % of the HDAC inhibitor is provided in the immediate release form and the remainder of the HDAC inhibitor is provided in the extended release form.

In further embodiments of the pharmaceutical composition according to the first aspect of the present invention 5 weight %, 10 weight %, 15 weight %, 20 weight %, 25 weight %, 30 weight %, 35 weight %, 40 weight %, 45 weight %, 50 weight %, 55 weight %, 60 weight %, 65 weight %, 70 weight %, 75 weight %, 80 weight %, 85 weight %, 90 weight %, or 95 weight % of the HDAC inhibitor is provided in the immediate release form and the remainder of the HDAC inhibitor is provided in the extended release form.

Presently preferred is that 70-90 weight % of the HDAC inhibitor is provided in the immediate release form and the remainder of the HDAC inhibitor is provided in the extended release form.

Specifically 70 weight %, 75 weight %, 80 weight %, 85 weight %, or 90 weight % may be provided in the immediate release form and the remainder of the HDAC inhibitor be provided in the extended release form.

It is however contemplated within the context of the present invention that this interval could be extended to 60-95 weight % of the HDAC inhibitor being provided in the immediate release form and the remainder of the HDAC inhibitor being provided in the extended release form.

Thus it is contemplated that 60 weight %, 65 weight %, 70 weight %, 75 weight %, 80 weight %, 85 weight %, 90 weight %, or 95% weight % of the HDAC inhibitor may be provided in the immediate release form and the remainder of the HDAC inhibitor be provided in the extended release form.

If there are more than one different HDAC inhibitors in the pharmaceutical composition according to the first aspect of the present invention, then the weight %, and the above mentioned remainder, mentioned in this description relates to the total amount, by weight, of HDAC inhibitors in the composition.

In a preferred embodiment of the pharmaceutical composition according to the first aspect of the present invention 75-85 weight %, such as 75 weight % of the HDAC inhibitor is provided in the immediate release form and the remainder of the HDAC inhibitor is provided in the extended release form.

This allocation of the HDAC inhibitor to the immediate release form and the extended release form has been has been shown to cause a plasma concentration, of the HDAC inhibitor, which quickly rises to, or above, the desired concentration, see the conclusion of the Example section.

In a preferred embodiment of the pharmaceutical composition according to the first aspect of the present invention both the immediate release form and the extended release form are formulated to release the HDAC inhibitor after passing the pyloric sphincter, such as in the small intestine, after having been taken orally by a human subject.

This encompasses formulating the immediate release form and the extended release form so that the HDAC inhibitor is released after passing the stomach, such as in the upper tract of the intestine.

The immediate release form and the extended release form may be formulated for this purpose by being enteric coated or by mixing materials used for enteric coatings with the HDAC inhibitors.

In a preferred embodiment of the pharmaceutical composition according to the first aspect of the present invention the extended release form comprises enteric coated granulates or enteric coated microgranulates.

This provides a simple implementation of the pharmaceutical composition according to the first aspect of the present invention. If further the immediate release form comprises granulates or microgranulates which are not enteric coated, then the pharmaceutical composition may easily be implemented as a single capsule comprising both the coated and non-coated granulates and or microgranulates.

In other embodiments of the pharmaceutical composition according to the first aspect of the present invention the extended release form comprises a matrix of insoluble substance in which the HDAC inhibitor is embedded so that the HDAC inhibitor must find its way out through the voids in the matrix before being released. In a variant of this embodiment the matrix is configured to swell whereby the swelling further affects the rate at which the HDAC inhibitor is released. In still further embodiments of the pharmaceutical composition according to the first aspect of the present invention the extended release form comprises a polymer-based tablet or body with a laser-drilled hole on one side and a porous membrane on the other side. Stomach acids push through the porous membrane, thereby pushing the HDAC inhibitor out through the laser-drilled hole.

In still further embodiments of the pharmaceutical composition according to the first aspect of the present invention the extended release form comprises microspheres having an inert core onto which one or more layers of the HDAC inhibitor and one or more layers of an insoluble or slowly soluble substance are coated.

In still further embodiments of the pharmaceutical composition according to the first aspect of the present invention the pharmaceutical composition may be formulated as a bilayer tablet where the immediate release form is in one layer and wherein the extended release form is in the other layer.

In a preferred embodiment of the pharmaceutical composition according to the first aspect of the present invention the enteric coated granulates or enteric coated microgranulates have a maximum dimension 500-1000 μm, such as 600-800 or 700 μm.

This range of maximum diameters ensures that the granulates pass through the stomach in the manner of a liquid, i.e. without being hindered by the activities of the pyloric sphincter.

The granulates are preferably spherical or oblong.

In one embodiment of the pharmaceutical composition according to the first aspect of the present invention the HDAC inhibitor is selected from the group consisting of vorinostat, romidepsin, valproic acid, aspanobinostat, panobinostat, belinostat, entinostat and resminostat.

In the preferred embodiment of the pharmaceutical composition according to the first aspect of the present invention the HDAC inhibitor is selected from the group consisting of valproic acid or valproate semisodium, sodium valproate or magnesium valproate.

In preferred embodiments of the pharmaceutical composition according to the first aspect of the present invention the pharmaceutical composition further comprises a steroid or a salt thereof, wherein the steroid is selected from the group consisting of prednisone, prednisolone, dexamethasone and betamethasone.

In the preferred embodiment of the pharmaceutical composition according to the first aspect of the present invention the HDAC inhibitor is valproic acid and the steroid is prednisone.

In the preferred embodiment of the pharmaceutical composition according to the first aspect of the present invention the steroid is provided in the immediate release form.

In this case the immediate release form should be formulated to release the HDAC inhibitor and the steroid in the small intestine of the upper tract of the intestine, for example by being formulated as granulates or microgranulates having a maximum dimension of 500-1000 μm and by being enteric coated.

In embodiments of the pharmaceutical composition according to the first aspect of the present invention the pharmaceutical composition may further comprise a pharmaceutically acceptable additive, diluent, carrier, excipient or buffer. Such pharmaceutically acceptable additives, diluents buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffering agents are magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The term "diluent" is intended to mean an aqueous or non-aqueous solution with the purpose of diluting the compounds in the pharmaceutical preparation. The diluent may be one or more of saline, water, polyethylene glycol, propylene glycol or ethanol.

The excipient may be one or more of carbohydrates, surfactants, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinyl alcohol/polyvinyl acetate of different degree of hydrolysis, and polyvinyl pyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In embodiments of the pharmaceutical composition according to the first aspect of the present invention the pharmaceutical composition is in the form selected from the group consisting of granulates, powders, tablets, coated tablets, microcapsules, microgranulates and effervescent forms.

The granulates, microgranulates and powders may comprise first and second types of granulates, microgranulates and powders where the immediate release form comprises the first type and the extended release form comprises the second type.

The granulates and microgranulates may be collected in a capsule or microcapsule.

Alternatively the granulates and microgranulates may be collected in a sachet. The sachet may be broken open to release the granulates and microgranulates for mixing with a liquid for drinking.

The powders may for example be pressed into tablets, which tablets may further be coated. The tablets may comprise at least one additive selected from the group comprising binders, lubricants, emulsifiers fillers, surfactants (e.g., polysorbate 80 and sodium lauryl sulfate), flavours, aromas (examples of ingredients giving taste) (such as orange, lemon, bergamon, grapefruit, banana, apricot and strawberry) and colours, including natural or synthetic ones, vitamins, sweeteners (examples of ingredients giving taste) (acesulfame potassium, sodium saccharin, aspartame, stevia and surcalose), nutritional additives (e.g antioxidants, peptides), and mixtures thereof.

Additionally the tablets may contain various lubricants suitable for use in the composition including water dispersible, water soluble, water insoluble lubricants and combinations thereof. Examples of useful water soluble lubricants include sodium benzoate, polyethylene glycol, L-leucine, adipic acid, and combinations thereof.

The tablets may also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof.

In one embodiment of the pharmaceutical composition according to the first aspect of the present invention the pharmaceutical composition comprises an effervescent form. Effervescence is the reaction (in water) of acids and bases producing carbon dioxide. Examples of acids used in this reaction are citric acid, tartaric acid, malic acid, fumaric acid, adipic acid, acid citrates, succinic acid and mixtures thereof. Citric acid is the most commonly used, and it imparts a citrus-like taste to the product. Examples of bases used in the effervescent reaction are sodium carbonate, potassium carbonate, sodium bicarbonate, potassium bicarbonate, calcium bicarbonate, magnesium carbonate, sodium glycocarbonate, carboxylysine and mixtures thereof. Sodium bicarbonate is very common in effervescent formulas.

The pharmaceutical composition according to the first aspect of the present invention is preferably formulated for systemic administration. Consequently the preferred administration routes are oral administration and parenteral (intravenous, subcutaneous, and intramuscular) administration.

A second aspect of the present invention relates to a device selected from the group consisting of a vial, ampule, pouch or infusion bag comprising the pharmaceutical composition according to the first aspect of the present invention.

By providing a device comprising the pharmaceutical composition according to the first aspect of the present invention it becomes easier to handle and administer the pharmaceutical composition.

A third aspect of the present invention relates to a kit comprising a number of doses of an HDAC inhibitor, a pharmaceutically acceptable acid or a salt thereof or a mixture of the acid and the salt, provided in both an immediate release form and in an extended release form wherein 70-90 weight % of the HDAC inhibitor is provided in the immediate release form and the remainder of the HDAC inhibitor is provided in the extended release form in at least one dose of the number of doses.

The kit according to the third aspect of the present invention is useful for providing and maintaining an effective concentration of the HDAC inhibitor during one session of pretreating cancer. The one session of pretreating cancer may for example comprise a time period of at least 12 hours such as 24 hours or at least 36 hours or at least 48 hours, and less than 96 hours such as less than 84 hours, such as less than 72 hours.

Further, the kit according to the second aspect of the present invention makes it easier to perform pretreatment of cancer and increases the compliance with the pretreatment.

The kit preferably comprises a number of doses sufficient for administration of two doses per 24 hour period during the session of pretreating cancer. The number of doses in the kit may be from 2 up to 8 doses.

In a preferred embodiment of the kit according to the third aspect of the present invention each of the number of doses comprises a pharmaceutical composition according to the first aspect of the present invention or a device according to the second aspect of the present invention.

In the preferred embodiment of the kit according to the third aspect of the present invention the number of doses, and the amount of the HDAC inhibitor that is provided in the extended release form and in the immediate release form in each dose, are configured to provide at least a maintained desired concentration of the HDAC inhibitor in a human to whom the doses of the kit are administered sequentially during one session of pretreating cancer.

The session of pretreating cancer preferably starts 48 hours prior to the treatment of cancer begins.

Typically there are 6 doses. Typically 75% of the HDAC inhibitor is provided in the immediate release form in each dose.

In some embodiments of the kit according to the third aspect of the present invention the amount of the HDAC inhibitor that is provided in the extended release form and in the immediate release form differ between individual doses of the number of doses.

This is advantageous as it allows for pretreating cancer more effectively. In one embodiment the initial doses comprise a larger amount of the HDAC inhibitor provided in the immediate release form while the later doses comprise a larger amount of the HDAC inhibitor in the extended release form to achieve that the desired concentration is reached in a shorter time. In a refinement thereof the last doses are similar to the initial doses so that the concentration of the HDAC inhibitor quickly decreases at the end of the pretreating session.

At least one of the doses may further comprise a steroid or a salt thereof, wherein the steroid is selected from the group consisting of prednisone, prednisolone, dexamethasone and betamethasone. In this case the steroid need not be present in each dose.

In some embodiments of the kit according to the third aspect of the present invention the the number of doses are provided in a suitable container and/or with suitable packaging, and the kit preferably further comprises instructions for how and when to administer the doses.

Thus the kit may for example comprise one or more blisters for holding the doses.

Preferably the kit comprises a blister pack comprising a plurality of collapsible blisters sealed by a frangible sealing sheet, each of the blisters holding one or more doses.

The kit may further include additional parts, including, for example, appropriate solutions for dilution (e.g., physiological saline solution, glucose solution, etc.), reagents (e.g., for adjusting pH), and devices (e.g., bags, tubes, syringes, needles, transfer sets) for assembly and use.

In some embodiments of the kit according to the third aspect of the present invention the kit comprises a number of doses sufficient for a plurality, such as 6, sessions of pretreating cancer. Also in this embodiment the amount of the HDAC inhibitor that is provided in the extended release form and in the immediate release form may differ, within the doses for one of the sessions and/or between the doses of different sessions, between individual doses of the number of doses.

Thus a single kit may be used for all doses needed for a typical cycle of treating cancer consisting of six sessions 14-21 days apart, wherein in each session the HDAC inhibitor is administered as pretreatment prior to other chemotherapy or immunotherapy.

Corresponding fourth and fifth aspects of the present invention relate to an HDAC inhibitor, a pharmaceutically acceptable acid or a salt thereof or a mixture of the acid and the salt, for use in a method of pretreating cancer, wherein the HDAC inhibitor, the pharmaceutically acceptable acid or the salt thereof or the mixture of the acid and the salt is provided in both an immediate release form and in an extended release form, wherein 70-90 weight % of the HDAC inhibitor is provided in the immediate release form and the remainder of the HDAC inhibitor is provided in the extended release form, wherein the HDAC inhibitor is administered to a human suffering from cancer, and a method of pretreating cancer comprising administrating an HDAC inhibitor, a pharmaceutically acceptable acid or a salt thereof or a mixture of the acid and the salt, provided in both an immediate release form and in an extended release form, wherein 70-90 weight % of the HDAC inhibitor is provided in the immediate release form and the remainder of the HDAC inhibitor is provided in the extended release form, to a human suffering from cancer, respectively.

The HDAC inhibitor, the pharmaceutically acceptable acid or the salt thereof or the mixture of the acid and the salt, may be provided in a composition, such as a pharmaceutical composition.

In the context of the present invention pretreatment and pretreating refer to treatment and treating performed prior to a subsequent treatment for the purpose of enhancing the effect, or mitigate the side-effects, of the subsequent treatment or treating. In the context of the present invention pretreatment is to be understood as a treatment performed prior to other treatments to enhance the effect, or mitigate the side-effects, of the other treatments. More particularly pretreatment of cancer encompasses sensitizing cancer cells prior to these cells being treated with other treatments thereby enhancing the effect of the other treatments. The pretreatment itself typically has only a limited effect on the cancer cells. Rather it is the combination of the pretreatment and the other treatments that provide an effective treatment of the cancer cells.

The administration of the HDAC inhibitor is preferably systemic, such as by oral administration or parenteral (intravenous, subcutaneous, and intramuscular) administration.

The HDAC inhibitor, the pharmaceutically acceptable acid or salt thereof or the mixture of the acid and the salt, provided in both the immediate release form and in the extended release form, should be administered in a pharmaceutically effective dose. By "Pharmaceutically effective dose" is meant a dose that is sufficient to produce the desired effects in relation to the condition for which it is administered. The exact dose is dependent on the manner of administration, the nature and severity of the disorder, and on the general health, sex, age and body weight of the patient. The total amount of the HDAC inhibitor, as well as the amount of the HDAC inhibitor that is provided in the immediate release form and the extended release form, respectively, as well as the number of doses and the time interval between the doses, should be selected so as to provide a plasma concentration of the HDAC inhibitor in the patient at or above the desired concentration for the specific HDAC inhibitor.

The desired concentration for e.g. Valpropic acid corresponds to a plasma concentration of 500 to 1500 µM, such as preferably 600 to 1000 µM. However it is expected that plasma concentrations of 500 to 2500 µM may be reached during the pretreatment.

As shown in the example, these levels may be reached by dosing valproic acid (including sodium valproate and valproate semisodium) in a dose lower than 60 mg/kg(body weight)/day.

In one example the HDAC inhibitor is administered once daily, such as during morning time, about 5 to 8 in the morning. However, the administration of the HDAC inhibitor may occur 1, 2, 3, 4 or even up to 5 times daily. The administration of the HDAC inhibitor may be at least 24-72 hours prior to the treatment, e.g. immune and/or chemotherapy, such as 30-60, 40-50 or 48 hours prior to the treatment.

The total amount of the HDAC inhibitor administered in a dose also depends on the identity of the HDAC inhibitor.

Accordingly, valproic acid may be administrated orally or intravenously in ranges from about 500 mg to about 15000 mg per day, such as from about 4000 mg to about 15000 mg per day, such as from about 400 mg to about 3000 mg per day. For example, oral dosages can be about 800, about 1600, about 2400, about 3000, about 6000, about 9000, about 15000 mg per day. The amount may be administered in one or more doses. Preferably the HDAC inhibitor is dosed based on the body surface area of the human. The body surface area of the human is preferably calculated using the following formula (Dubois & Dubois): $0.20247 \times \text{height (m)}^{0.725} \times \text{weight (kg)}^{0.425}$.

Belinostat may be administrated orally in ranges from about 6 mg to about 3000 mg per day, such as from about 40 mg to about 3000 mg per day, such as from about 400 mg to about 3000 mg per day. For example, oral dosages can be about 4, about 40, about 400, about 800, about 1600, about 2400, about 2800 or about 3000 mg per day. The amount may be administered in one or more doses.

In some embodiments of the HDAC inhibitor for use according to the fourth aspect of the present invention, and the method according to the fifth aspect of the present invention, a steroid or a salt thereof, wherein the steroid is selected from the group consisting of prednisone, prednisolone, dexamethasone and betamethasone, is also administered to the human suffering from cancer.

Prednisone or prednisolone may be administered in an amount of 20 to 200 mg per day, such as 50-200, 100-150, 30, 40, 50, 60, 70, 80, 90, 100, 110, 120, 130, 140, 150, 160, 170,180, 190 or 200 mg per day. The amount may be administered in one or more doses Betamethasone may be administered in an amount of 4 to 32 mg per day, such as 10-25, 10-20, 5, 6, 7, 8, 9, 10, 11, 12, 13, 14, 15, 16, 17, 18, 19, 20, 21, 22, 23, 24, 25, 26, 27, 28, 29, 30, 31 or 32 mg per day. The amount may be administered in one or more doses.

Dexamethasone may be administered in an amount of 10 to 80 mg per day, such as 20-70, 10, 20, 30, 40, 50, 60, 70 or 80 mg. The amount may be administered in one or more doses.

In some embodiments of the HDAC inhibitor for use according to the fourth aspect of the present invention and the method according to the fifth aspect of the present invention the HDAC inhibitor is provided as a composition according to the first aspect of the present invention, as a device according to the second aspect of the present invention, or as a kit according to the third aspect of the present invention.

In further embodiments of the HDAC inhibitor for use according to the fourth aspect of the present invention and the method according to the fifth aspect of the present invention the cancer is selected from the croup consisting of sarcoma, malignant melanoma, skin cancer, estrogen receptor-dependent and independent breast cancer, ovarian cancer, prostate cancer, renal cancer, colon and colorectal cancer, pancreatic cancer, head and neck cancer, small cell and non-small cell lung carcinoma, and cancer of blood cells.

In preferred embodiments of the HDAC inhibitor for use according to the fourth aspect of the present invention and the method according to the fifth aspect of the present invention the cancer is selected from the croup consisting of diffuse large B cell lymphoma (DLBCL), follicular lymphoma, chronic lymphocytic leukaemia, T cell lymphoma, myeloma and Hodgkin lymphoma.

In some embodiments of the HDAC inhibitor for use according to the fourth aspect of the present invention and the method according to the fifth aspect of the present invention the human is treated with chemotherapy and/or immunotherapy after the pretreating.

The chemotherapy and/or immunotherapy should be selected based on the type of cancer that the human is suffering from.

The chemotherapy may comprise administration of CHOP, a combination of cyclophosphamide, doxorubicin, vincristine and prednisone, which may be administered in amounts of 750+/−10% mg/m$^2$ of cyclophosphamide, 50+/−10% mg/m$^2$ of doxorubicin, 1.4+/−10% mg/m$^2$ of vincristine and 50+/−10% mg/m$^2$ of prednisone, wherein m$^2$ refers to the body surface of the human.

The immunotherapy may comprise administering an antibody, monoclonal antibody or a functional fragment thereof, such as Rituximab, ofatumumab, GA101, tositumumab, ibritumumab, ocraluzumab, veltuzumab, epratuzumab, FTBA05, AME-133V or R603. All the above mentioned antibodies bind to CD20 present on B-cells. The antibodies may be administrated in an amount of 375+/−10% mg/m$^2$.

Other examples of treatment that may follow the pretreating comprise surgery, radiation, and gene therapy.

In preferred embodiments of the HDAC inhibitor for use according to the fourth aspect of the present invention and the method according to the fifth aspect of the present invention the HDAC inhibitor is administered twice or thrice daily.

In alternative embodiments of the HDAC inhibitor for use according to the fourth aspect of the present invention and the method according to the fifth aspect of the present invention the HDAC inhibitor is administered as a single daily dose.

In further embodiments of the HDAC inhibitor for use according to the fourth aspect of the present invention and the method according to the fifth aspect of the present invention the method comprises at least two sessions of pretreating and the plasma concentration of the HDAC inhibitor is determined after the first session of pretreating and used to adjust the total amount of the HDAC inhibitor, and/or the amount of the HDAC inhibitor provided in the immediate release form and in the extended release form, administered to the human during the second session of pretreating.

This is advantageous to prevent the better metabolism of the HDAC inhibitor during the second session of pretreating, i.e. when the body of the human suffering from cancer recognizes the HDAC inhibitor and thereby metabolizes it fast, from causing a too low plasma concentration of the HDAC inhibitor during the second session of pretreating. By suitably adjusting the total amount of the HDAC inhibitor, and/or the amount of the HDAC inhibitor provided in the immediate release form and in the extended release form, administered to the human during the second session of pretreating, for example by increasing the total amount, it can be ensured that the plasma concentration of the HDAC inhibitor during the second session of pretreating remains at or above the desired concentration.

Corresponding sixth and seventh aspects of the present invention relate an HDAC inhibitor, a pharmaceutically acceptable acid or salt thereof or a mixture of the acid and salt, for use in a method of combination treatment of cancer, wherein the HDAC inhibitor, the pharmaceutically acceptable acid or salt thereof or the mixture of the acid and salt is provided both in an immediate release form and in an extended release form, wherein 70-90 weight % of the HDAC inhibitor is provided in the immediate release form and the remainder of the HDAC inhibitor is provided in the extended release form, in combination with one or more chemotherapeutic or immunotherapeutic compositions, and a method of combination treatment of cancer comprising performing the method of pretreating cancer according to the fifth aspect of the present invention before performing one or more treatments of cancer.

The one or more treatments of cancer may be chemotherapy and/or immunotherapy as discussed above in connection with the fourth and fifth aspect of the present invention.

In a further embodiment of the HDAC inhibitor for use according to the sixth aspect of the present invention and the method according to the seventh aspect of the present invention the HDAC inhibitor is used in combination with an immunotherapeutic composition comprising monoclonal antibodies such as rituximab or other CD-20 binding antibodies.

The eight aspect of the present invention relates to a dispenser for dispensing pharmaceuticals from a blister pack comprising a plurality of collapsible blisters sealed by a frangible sealing sheet, the dispenser comprising:

a lower housing portion comprising a plurality of apertures, and an upper housing portion joined to the lower housing part, the upper housing part comprising an elongated aperture defining a serpentine track sequentially running past each aperture of said plurality of apertures, whereby the lower housing portion and the upper housing portion define, between them, a cavity configured for receiving a blister pack such that the sealing sheet is oriented towards the lower housing portion and such that the blisters are oriented towards the upper housing portion and aligned with the plurality of apertures, the dispenser further comprising:

a press part extending from within the cavity to outside the cavity through the elongated opening in the upper housing part, the press part being configured for being moveable along the serpentine track for sequentially physically striking and collapsing the plurality of blisters of the blister pack when the blister pack is received in said cavity.

The lower housing portion and the upper housing portion are preferably joined at their circumferential edges to each other. Alternatively the lower housing portion and the upper housing portion may be formed integrally with each other.

The plurality of apertures is preferably 6 to 10 apertures. The apertures may be square or circular and should be configured to correspond to the dimension and shape of the blisters.

The elongated aperture preferably has a width that is smaller than the diameter of the apertures.

Preferably the elongated aperture is arranged such that the serpentine track passes no more than two adjacent apertures before changing direction. This is advantageous as it requires the press part to be moved in a new direction each time the contents of a blister is to be dispensed, thus preventing dispensing the contents of more than one blister at a time.

The cavity may be configured for receiving the blister pack by having inner dimensions at least as large as the outer dimension of the blister pack.

The press part may comprise a press plate provided within the cavity and a press handle extending to outside the cavity. The press plate may for example be arranged to lie flush with the ceiling of the cavity and the press handle may comprise a stem having a diameter configured to allow it to pass through the elongated aperture and a handle or button attached to the stem outside the dispenser.

The press part may be configured for being moveable along the serpentine track by ensuring that the diameter of the press part as it passes through the elongated aperture is smaller than the width of the elongated aperture, and by ensuring that the part of the press plate within the cavity does not strike the walls of the cavity when the press part is moved along the serpentine track.

As the press part sequentially physically strikes and collapses the plurality of blisters the medication, i.e. the tablet(s), capsules(s) or other content in the blisters are forced out of the blisters, through the sealing sheet which ruptures, to fall out by gravity from the dispenser through the apertures in the lower housing part.

The dispenser according to the eight aspect of then present invention is preferably used together, i.e. in combination, with a blister pack-embodiment of the kit according to the third aspect of the present invention, i.e. where the kit comprises a blister pack comprising a plurality of collapsible blisters sealed by a frangible sealing sheet, each of the blisters holding one or more doses. In this blister pack-embodiment the first blister may contain the dose/doses to be administered on the morning of the first day of pretreatment, the second blister may contain the dose/doses to be administered on in evening of the first day of pretreatment, the third blister may contain the dose/doses to be administered on the morning of the second day of pretreatment, and so on. With this combination patient compliance is increased, and there is less risk of taking the doses in the wrong order as the dispenser only allows the blisters of the blister pack to be collapsed in the correct order, i.e. first blister, second blister, third blister, and so on.

A preferred embodiment of the dispenser according to the eight aspect of the present invention will now be described in more detail with reference to FIGS. 1-5.

Figure 1:
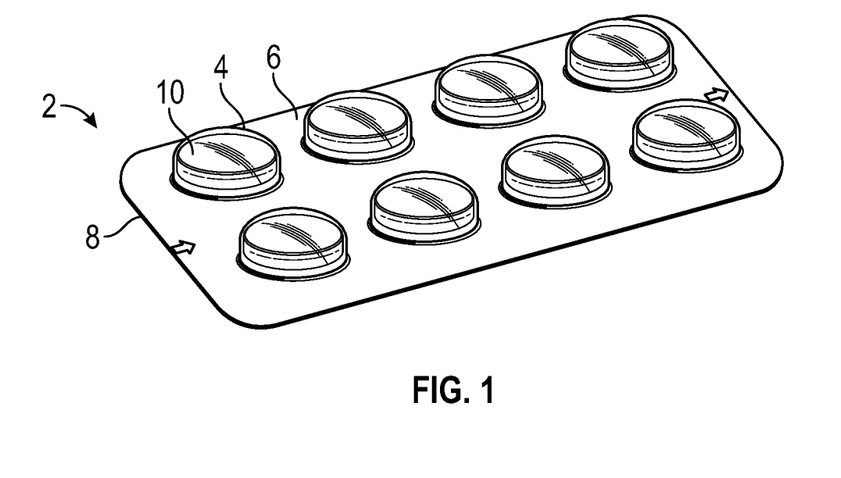
FIG. 1 shows a blister pack comprising a number of doses of the composition according to the first aspect of the present invention.

FIG. 1 shows a generally planar blister pack 2 comprising a plurality of, in this case, optically clear plastic blisters, one of which is designated the reference numeral 4. The blisters 4 are formed from a plastic sheet 6 and sealed on the underside by sealing sheet in the form of an aluminum foil 8. Each blister 4 comprises a dose such as a dose of the composition according to the first aspect of the present invention, in this case in the dosage form of a tablet 10.

The use of blister packs for packaging and preserving pharmaceuticals is as such conventional; however there is always a risk with blister packs that more than one blister is collapsed, for example by mistake, at the same time.

Figure 2:
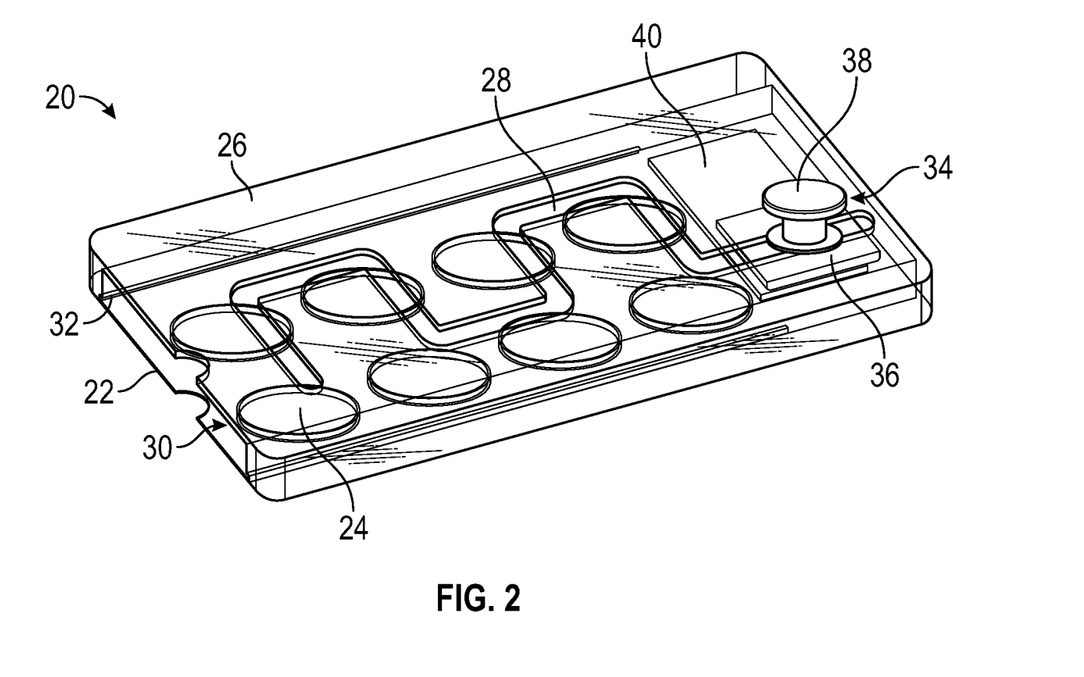
FIG. 2 shows a dispenser according to the eight aspect of the present invention.

FIG. 2 shows a preferred embodiment of a dispenser 20 according to the eight aspect of the present invention. The dispenser 20 comprises a generally planar lower housing part 22 comprising a plurality of apertures, one of which is designated the reference numeral 24, and a generally planar upper housing part 26 comprising an elongated aperture 28 defining a serpentine track 28. Between the housing parts 22 and 26 is defined a cavity 30 for receiving the blister pack 2. Conveniently, but not necessarily, the dispenser 20 comprises, in the lower housing part 22, the upper housing part 26, or between them, elongated parallel tracks or grooves, one of which is designated the reference numeral 32 for guiding the longitudinal edges of the blister pack 2.

Also provided in one end of the dispenser is a press part 34 extending from within the cavity 30, from a press foot or press plate 36, to outside the cavity 30 through the elongated aperture 28 to a press handle 38. The cavity 30 is divided into a first part, into which the blister pack 2 is received, and into a second part, in which the press part 34 may be "parked" on a support 40 when no blister pack 2 is in the dispenser 20.

As is clearly shown in FIG. 2 the elongated aperture 28 and the serpentine track defined by it passes each of the apertures 24, sequentially, in the lower housing part 22. The serpentine track passes a maximum of two (2) adjacent apertures 24 before making a 90° turn.

Figure 3:
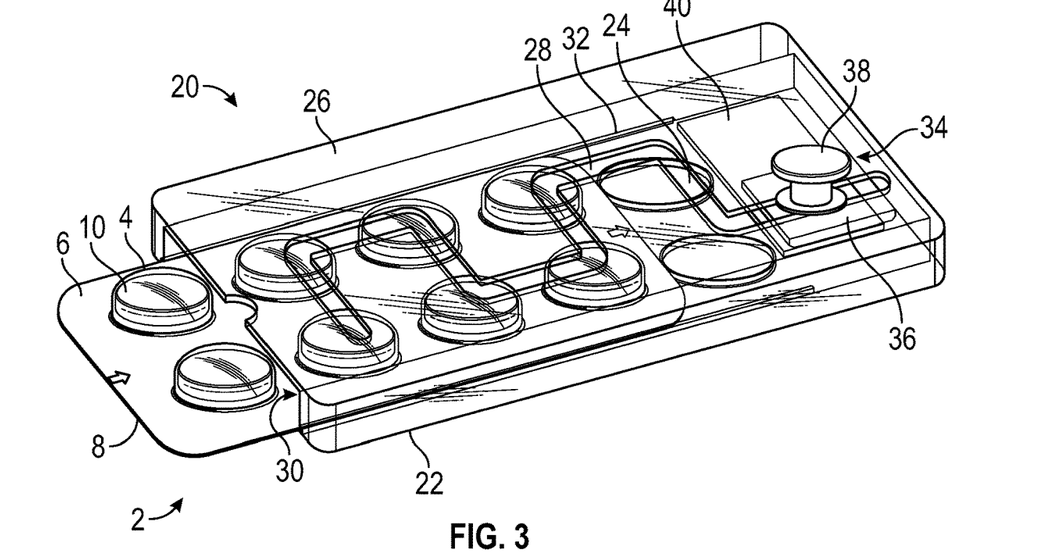
FIG. 3 shows the blister pack being inserted into the dispenser.

FIG. 3 shows the blister pack 2 at a point where it has been inserted ¾ of its length into the cavity 30 of the dispenser 20. As is seen from the figure the blisters 6 line up with the apertures 24, further it is seen that the apertures 24 are dimensioned so as to allow the contents of the blisters 4, i.e. the tablet 10, to pass through.

Figure 4:
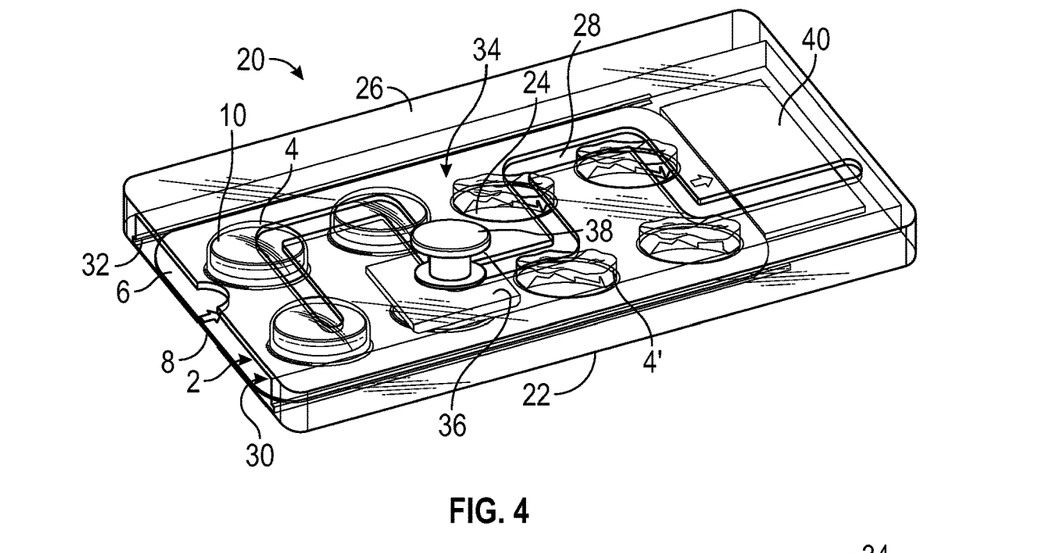
FIG. 4 shows how the dispenser has been used to dispense a number of the doses in the blister pack.
Figure 5:
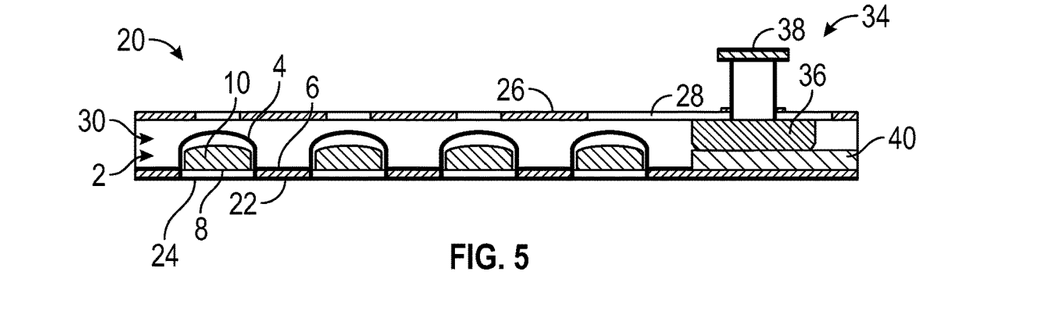
FIG. 5 shows, in cross section, the blister pack inserted into the dispenser.

The functioning of the dispenser 20 will now be evident from FIG. 4 and FIG. 5. In FIG. 4 the patient, or the user of the dispenser 20, has moved the press part 34 along the serpentine track a total of five times, thus dispensing the contents of five of the blisters 4. When moving the press part 34 to a new position along the serpentine track the press plate 36 engages and collapses the blisters 4 thus forcing the contents of the blister 4, i.e. the tablet 10, out of the blister 4 through the aluminum foil 8, which aluminum foil ruptures, and through the aperture 24 corresponding to the blister 4 being collapsed. See for example the now empty collapsed blister 4'. Particularly, because of the fact that the serpentine track only passes a maximum of two apertures 24 before making a 90° turn only one blister 24, and consequently only one table 10, can be dispensed each time. This prevents that multiple blisters are collapsed and multiple tablets 10 are dispensed at the same time, further it provides ensuring that the tablets 10 are taken in the correct order, meaning that if for example the odd-numbered blisters (1, 3, 5, 7) comprise tablets to be taken in the morning, and if the even-numbered blisters (2, 4, 6, 8) comprise tablets to be taken in the evening, there is less risk of taking the tablets in the wrong order. Once all blisters 4 of the blister pack 2 have been collapsed the blister pack 2 is easily withdrawn from the cavity 30 and a new blister pack is inserted in its stead.

In a further aspect of the present invention a HDAC inhibitor as described above, preferably valproic acid, sodium valproate or valproate semisodium, may be used in a method of pretreating arthritis, wherein the HDAC inhibitor is administered to a patient suffering from arthritis before a CD-20 specific monoclonal antibody, such as rituximab, is administered to the patient.

The HDAC inhibitor may be formulated according to the first aspect of the present invention, or provided as a device or kit according to the second and third aspects of the present invention.

Administering the HDAC inhibitor as a pretreatment of arthritis increases the efficiency of the following treatment of the arthritis with the CD-20 specific monoclonal antibody.

EXAMPLE 1

Simulation of valproate (VPA) plasma concentrations after oral administration of different compositions of multiple-unit enteric coated modified release formulations.

Valproic acid was used as an example of a HDAC inhibitor in simulations of compositions according to the first aspect of the present invention. The simulations were performed by the companies ES Health & Pharmaceutics AB (Uppsala, Sweden) and Hans Lennernas BioMedical AB (Uppsala, Sweden) in 2016.

Background

Valproic acid (VPA) (MW 144.2; log P 2.8, PSA=37.3 Å$^2$) has been reported to be rapidly and completely absorbed in the gastrointestinal (GI) tract after oral administration. The bioavailability (F) is high (close to 100%) for immediate release, modified release and extended release formulations indicating low first-pass extraction in the gut and liver (Dutta and Zhang—Biopharm. Drug Dispos. 25 (8), 345-352, 2004; Chun et al., J. Clin. Pharmacol. 20 (1), 30-36, 1980; Carrigan et al., J. Clin. Pharmacol. 30 (8), 743-747, 1990; Fischer et al., Neurology 38 (8), 1319-1322, 1988). Intestinal absorption of VPA has been measured by deconvolution up to 22 hr indicating that VPA is absorbed along the total length of the GI-tract, including colon (Dutta and Zhang, 2004). VPA has been reported to readily soluble in water (50 mg/ml according to Sigma-Aldrich). Based on these reported values VPA is classified according to the biopharmaceutical classification system (BCS) as a class I compound (Amidon et al, Pharm Res. 1995 March; 12(3): 413-20, 1995).

Model Approach Applied

Figure 6A:
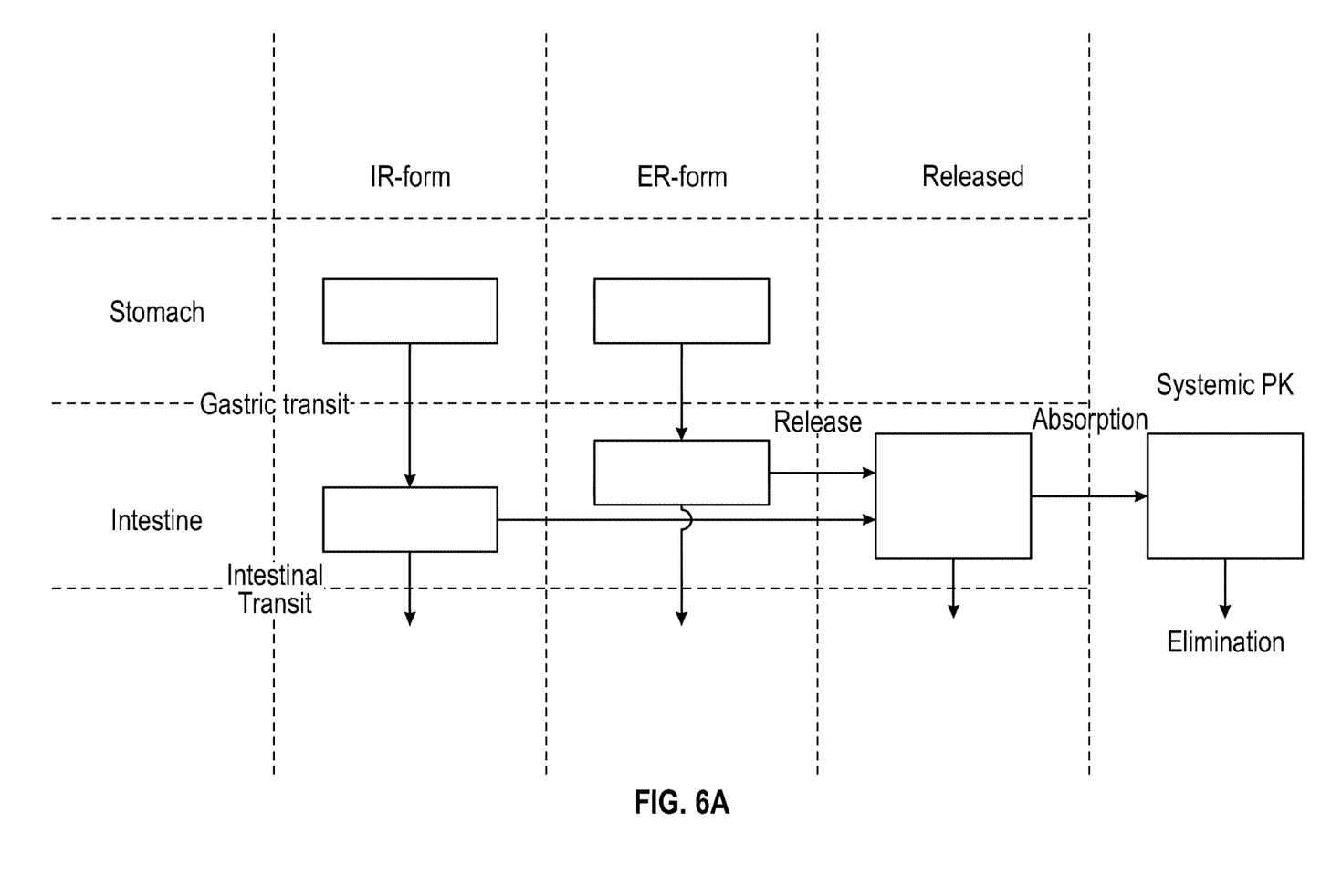
FIGS. 6A-6E show results from simulations of valproate (VPA) plasma concentrations after oral administration of different compositions of multiple-unit enteric coated modified release formulations.

A compartmental model structure was adopted to simulate the plasma-concentration profiles after oral administration of VPA, see FIG. 6A (Buxton et al., The Pharmacological Basis of Therapeutics, 12th ed, 2011; Teorell, Arch Int Pharmacodyn et Ther 57: 205-225, 1937). The model structure allowed simulating a formulation including one immediate release (IR) component and one extended release (ER) component. Simulations were performed with stomach emptying according to fasted or fed state. In the fasted state the gastric transit time was set to 15 min (1$^{st}$ order) according to fasted state transit of fluids (Sjogren et al., Eur J Pharm Sci. 2014 Jun. 16; 57:99-151 2014). In the fed state the transfer of material from the stomach to the intestines was set to 30% of dose/h (zero order)—according to the gastric transit of the chyme after consumption (chewed) of a standard meal (Olausson et al. Diabetes Res Clin Pract. 2008 May; 80(2): 231-7, 2008). Both formulation components were modelled to be enteric coated particulates, assumed to be transported along with the chyme, from which the drug was released whence reached the intestinal compartment. The transit time through both small and large intestine was set to 20 h (i.e., representing the absorption of VPA that occurs along the intestines except the terminal colon). The rate of absorption of released drug was modelled by a first order process ($k_{abs}$=61 h$^{-1}$) based on the data presented by Dutta and Reed, Epilepsy Res. 2007 March;73(3):275-83. Systemic plasma concentration was described by a one compartment model. Parameters describing the systemic pharmacokinetics (for a 70 kg person) were collected from literature, Vd=10.6 L, CL=0.61 L/h, F=100% (Gugler and Unruh, Clin Pharmacokinet. 1980 January-February; 5(1):67-83, 1980).

The hypothetical oral formulation for VPA that was evaluated in this simulation study was based on an IR part together with an ER part. The major objective of this simulation study was to determine the proportion of the total dose of VPA allocated to the two formulation parts. The different proportion was evaluated by simulating plasma concentration-time profiles. All simulations presented in this report were performed adopting first order release kinetics from the formulation components (immediate release (IR) and extended release (ER)) according to:

$$k\text{IR}=6 \text{ h}-1 \ (t\frac{1}{2}.\text{release}=7 \text{ min})$$

$$k\text{ER}=0.25 \text{ h}-1 \ (t\frac{1}{2}.\text{release}=170 \text{ min})$$

Model Evaluation

Figure 6B:
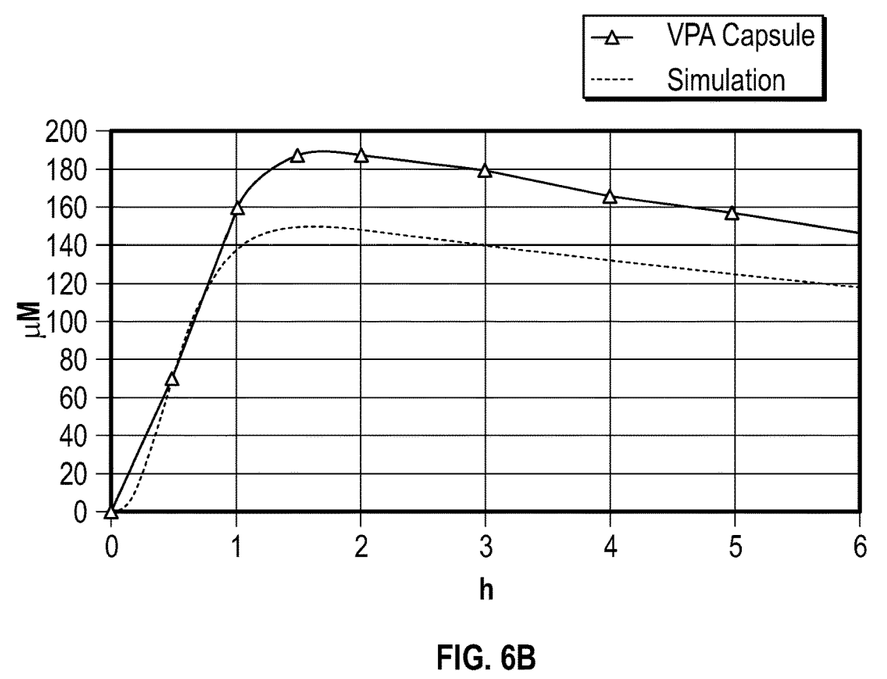
Figure 6C:
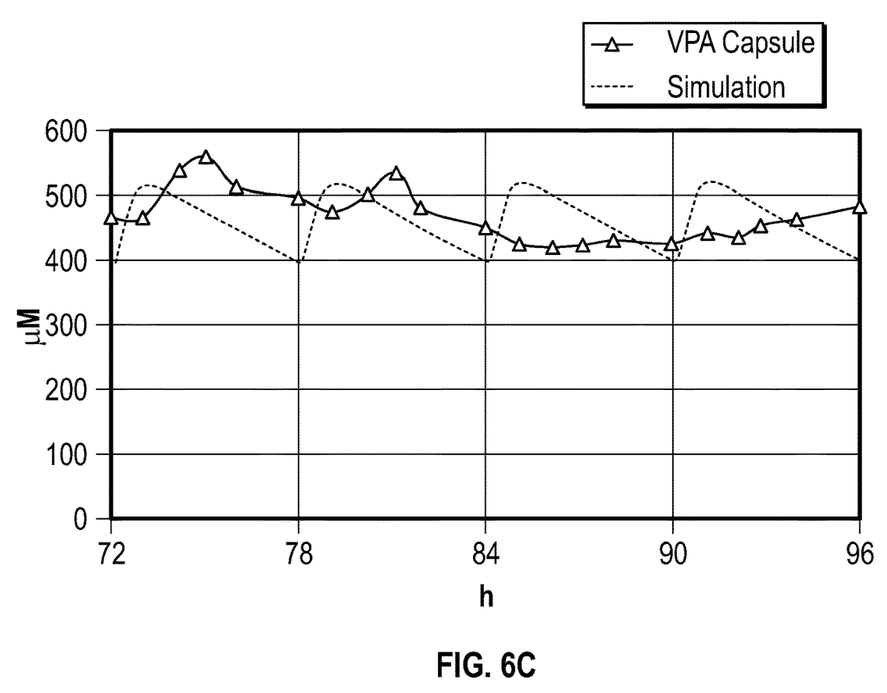

The accuracy of the fasted state model was briefly evaluated towards reported data of 250 mg VPA administered as single and repeated (every 6 hr=1000 mg per day) dose administration (Dutta and Reed 2007, Hussein et al., J Clin Pharmacol. 1994 July; 34(7):754-9, 1994), see FIGS. 6B and 6C. The systemic plasma concentration after repeated oral administration was well described. A slight underestimation compared to the single dose administration was acquired, likely caused by differences in systemic disposition pharmacokinetics (PK) (CL=0.52 L/h V=7.1 L). In all, the evaluation show that the model performs adequately well and that the systemic PK parameters adopted are valid. The evaluation was done with 100% IR in the model formulation.

Simulations

Figure 6D:
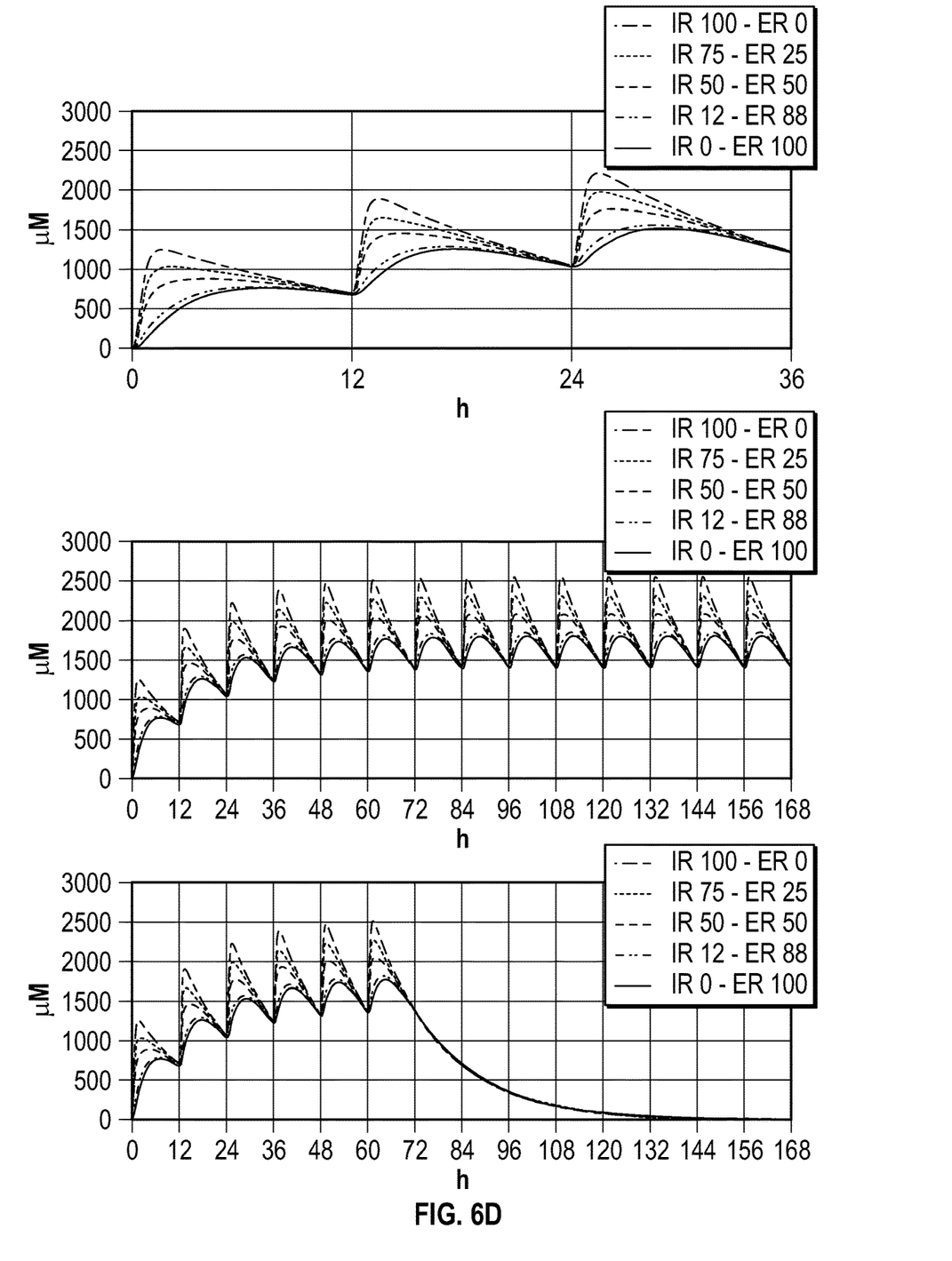
Figure 6E:
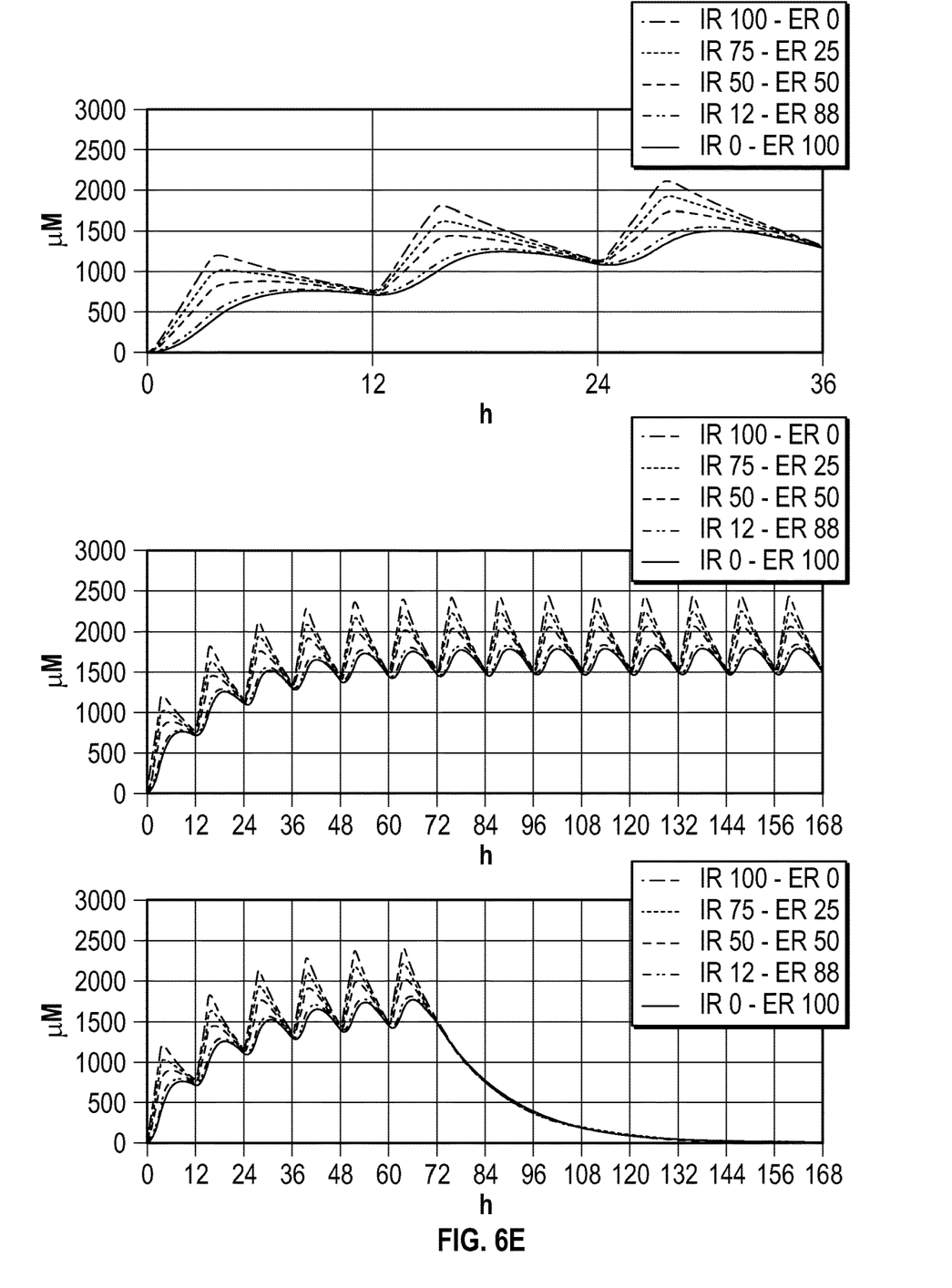

The systemic exposure of VPA in a 70 kg individual after oral administration in the fed state of a total dose VPA of 60 mg/kg/day given as a twice per day dosing regimen (2100 mg/12 h=14500 μmol/12 h) was simulated. Simulations were performed with the IR component representing 100%, 75%, 50%, 12% and 0% of the total dose, and the ER component representing the remaining dose in each case (0%, 25%, 50%, 88% and 100%). Results are presented after 3 (up to 36 h) and 14 (up to 168 h) consecutive doses as well as 3 days of treatment (6 doses)+4 days of washout for the two adopted gastric transit times settings for fasted (FIG. 6D) and fed state (FIG. 6E).

Conclusion

It is clear that VPA has excellent biopharmaceutical properties to be successfully formulated in a dual release formulation, including an extended release part, with absorption along the total length of the GI-tract, including colon.

The accuracy of the adopted model was shown by the ability to replicate VPA concentration time profiles of previously published studies.

In the fed state it is anticipated that if a VPA plasma concentration of 1000-600 µM is desired, then this plasma concentration is reached quickest after the first dose of a formulation with the IR/ER-relation of 75%/25%.

For the simulated dosage regimen (60 mg/kg/day) the concentration of VPA at steady state is predicted to fluctuate between 1500 and 2500 µM depending on the composition of the formulation. Decreasing the dose or prolonging the dose interval allows the concentration of VPA at steady state to be lowered so that it, while fluctuating, is above the desired minimum plasma concentration yet is not excessively higher than the desired concentration.

EXAMPLE 2

Sodium Valproate Capsules

The manufacturing of sodium valproate capsules consists of a series of consecutive unit operations: wet granulation, extrusion, spheronization, drying, coating and capsule filling. Each unit operation is described below.

Wet Granulation

The HDAC inhibitor sodium valproate is dry blended, by conventional means such as a planet blender or high-shear blender, together with cellulose of suitable quality (such as microcrystalline or powdered qualities) in a ratio delivering the necessary amount of drug in a suitable number of microgranules with regard to dosage strength, reproducibility of filling and acceptable capsule size. In order to facilitate the achievement of the desired release rates, other excipients such as lactose and/or starch, can be added to the dry blend. The dry blend is then converted into a moist paste by addition, under continuous mixing, of water only, or of water that contains binders such as povidone, methyl cellulose, hydroxypropyl cellulose etc.

Extrusion

The moist paste resulting from the wet granulation is shaped into cylinders by applying pressure to the paste, causing it to flow through orifices of a defined diameter. Suitable extrusion means are conventional extruders such as ram extruders or screw extruders etc.

Spheronization

The cylinders consisting of the sodium valproate/excipient blend are transferred into a spheronizer, which consists of a cylinder with a rotating disc at the bottom. As the bottom disc rotates at high speed, the cylinders are shaped into spherical microgranules. The diameter of the microgranules is defined by the diameter of the orifices used at the extrusion step.

Drying

The microgranules produced by the spheronization step are dried by conventional means, such as fluid bed drying, where the moisture level of the microgranules is reduced through the passing of heated air through the bed of microgranules.

Coating

The dry microgranules are divided into two sub-batches to be further processed into either IR (immediate release) or ER (extended release) microgranules. Both sub-batches are coated with a thin polymer layer, where the polymer is chosen to achieve the respective desired release property. For IR microgranules, a polymer suitable for enteric coating is used, such as commercially available acrylate/methacrylate copolymers (e.g. Eudragit L100) dispersed in a suitable aqueous or non-aquoeous medium. For IR microgranules, a polymer designed to slowly erode is used, such as commercially available ethylcellulose polymers (e.g. Aquacoat ECD), also dispersed within a suitable medium. Both IR and ER microgranules are coated by conventional means, such as a fluid bed coater, where a bed of microgranules is loaded into a conical vessel fitted with one or several spray nozzles. The microgranule bed is fluidized by allowing heated air to pass through, and consecutive layers of coating are applied by atomizing the polymer dispersion through said spray nozzles. The coating layer is gradually built up until the desired release properties of the coated microgranules are achieved.

Capsule Filling

IR and ER microgranules are filled into standard hard capsules in the desired, gravimetrically determined proportion as to achieve finished dosage units with the overall target release properties.

The invention claimed is:

1. A pharmaceutical composition comprising an HDAC inhibitor, a pharmaceutically acceptable acid or a salt thereof or a mixture of the acid and the salt, provided in both an immediate release form and in an extended release form wherein 70-90 weight % of the HDAC inhibitor is provided in the immediate release form and the remainder of the HDAC inhibitor is provided in the extended release form, wherein the HDAC inhibitor is selected from the group consisting of valproic acid, valproate semisodium, sodium valproate and magnesium valproate.

2. The pharmaceutical composition according to claim 1, wherein 75-85 weight %, of the HDAC inhibitor is provided in the immediate release form and the remainder of the HDAC inhibitor is provided in the extended release form.

3. The pharmaceutical composition according to claim 1, wherein both the immediate release form and the extended release form are formulated to release the HDAC inhibitor after passing the pyloric sphincter, after having been taken orally by a human subject.

4. The pharmaceutical composition according to claim 1, wherein the extended release form comprises enteric coated granulates or enteric coated microgranulates.

5. The pharmaceutical composition according to claim 4, wherein the enteric coated granulates or enteric coated microgranulates have a maximum dimension 500-1000 µm.

6. The pharmaceutical composition according claim 1, further comprising a steroid or a salt thereof, wherein the steroid is selected from the group consisting of prednisone, prednisolone, dexamethasone and betamethasone.

7. The pharmaceutical composition according to claim 6, wherein the steroid is provided in the immediate release form.

8. A kit comprising a number of doses of a pharmaceutical composition comprising an HDAC inhibitor, a pharmaceutically acceptable acid or a salt thereof or a mixture of the acid and the salt, provided in both an immediate release form and in an extended release form wherein 70-90 weight % of the HDAC inhibitor is provided in the immediate release form and the remainder of the HDAC inhibitor is provided in the extended release form in at least one dose of the number of doses, wherein the HDAC inhibitor is selected from the group consisting of valproic acid, valproate semisodium, sodium valproate and magnesium valproate.

9. The kit according to claim 8, wherein the number of doses and the amount of the HDAC inhibitor that is provided in the extended release form and in the immediate release form in each dose is configured to provide at least a maintained desired concentration of the HDAC inhibitor in a human to whom the doses of the kit are administered sequentially during one session of pretreating cancer.

10. A method of pretreating cancer comprising administrating a pharmaceutical composition to a human suffering from cancer, wherein the pharmaceutical composition comprises an HDAC inhibitor, a pharmaceutically acceptable acid or a salt thereof or a mixture of the acid and the salt, wherein the HDAC inhibitor, the pharmaceutically acceptable acid or the salt thereof or the mixture of the acid and the salt is provided in both an immediate release form and in an extended release form, wherein 70-90 weight % of the HDAC inhibitor is provided in the immediate release form and the remainder of the HDAC inhibitor is provided in the extended release form, wherein the HDAC inhibitor is selected from the group consisting of valproic acid, valproate semisodium, sodium valproate and magnesium valproate.

11. The method according to claim 10, wherein the human is treated with chemotherapy and/or immunotherapy after the pretreating.

12. The method according to claim 10, wherein the HDAC inhibitor is administered twice or thrice daily.

13. The method according to claim 10, wherein the HDAC inhibitor is administered as a single daily dose.

14. The method according to claim 10, wherein the method comprises at least two sessions of pretreating and wherein the plasma concentration of the HDAC inhibitor is determined after the first session of pretreating and used to adjust the total amount of the HDAC inhibitor, and/or the amount of the HDAC inhibitor provided in the immediate release form and in the extended release form, that is administered to the human during the second session of pretreating.

15. A method of combination treatment of cancer comprising combining the method according to claim 10 with the administration of one or more chemotherapeutic or immunotherapeutic compositions to the human suffering from cancer.

16. The method according to claim 15 wherein the one or more chemotherapeutic or immunotherapeutic compositions is an immunotherapeutic composition comprising a monoclonal antibody.

17. The method according to claim 10, wherein the cancer is selected from the croup consisting of diffuse large B cell lymphoma (DLBCL), follicular lymphoma, chronic lymphocytic leukaemia, T cell lymphoma, myeloma and Hodgkin lymphoma.

18. The pharmaceutical composition according to claim 2, wherein 75 weight % of the HDAC inhibitor is provided in the immediate release form and the remainder of the HDAC inhibitor is provided in the extended release form.

19. The pharmaceutical composition according to claim 3, wherein both the immediate release form and the extended release form are formulated to release the HDAC inhibitor in the small intestine.

20. The pharmaceutical composition according to claim 5, wherein the enteric coated granulates or enteric coated microgranulates have a maximum dimension 600-800 µm.

* * * * *